(12) United States Patent
Tieng et al.

(10) Patent No.: US 9,513,353 B2
(45) Date of Patent: Dec. 6, 2016

(54) ARRANGEMENT OF COILS FOR MRI APPARATUS

(75) Inventors: Quang Minh Tieng, Sinnamon Park (AU); Viktor Vegh, Coorparoo (AU); Ian Malcolm Brereton, Cholmer (AU)

(73) Assignee: THE UNIVERSITY OF QUEENSLAND, St. Lucia, Queensland (AU)

( * ) Notice: Subject to any disclaimer, the term of this patent is extended or adjusted under 35 U.S.C. 154(b) by 689 days.

(21) Appl. No.: 12/991,650

(22) PCT Filed: May 7, 2009

(86) PCT No.: PCT/AU2009/000572
§ 371 (c)(1),
(2), (4) Date: Feb. 17, 2011

(87) PCT Pub. No.: WO2009/135264
PCT Pub. Date: Nov. 12, 2009

(65) Prior Publication Data
US 2011/0133739 A1    Jun. 9, 2011

(30) Foreign Application Priority Data

May 8, 2008 (AU) .............................. 2008902243

(51) Int. Cl.
*G01R 33/381* (2006.01)
*A61B 5/055* (2006.01)
(Continued)

(52) U.S. Cl.
CPC .............. *G01R 33/381* (2013.01); *A61B 5/055* (2013.01); *G01R 33/3806* (2013.01); *G01R 33/3815* (2013.01)

(58) Field of Classification Search
CPC .............. G01R 33/381; G01R 33/3806; G01R 33/3815; A61B 5/055
See application file for complete search history.

(56) References Cited

U.S. PATENT DOCUMENTS 4,701,736 A   10/1987 McDougall et al.
5,309,107 A   5/1994 Pausch
(Continued)

FOREIGN PATENT DOCUMENTS

| EP | 1 074 852 A2 | 2/2001 |
|---|---|---|
| JP | 11-225990 | 8/1999 |
| WO | 2005/024443 | 3/2005 |

OTHER PUBLICATIONS

International Search Report for PCT/AU2009/000572, mailed Jul. 22, 2009.

(Continued)

*Primary Examiner* — Dixomara Vargas
(74) *Attorney, Agent, or Firm* — Nixon & Vanderhye P.C.

(57) ABSTRACT

A method of determining a magnet arrangement for use in magnetic resonance imaging apparatus, the method including, determining a function representing current densities required within a magnet region to generate a field, determining a current density distribution required to generate a desired field, using the function and determining the magnet arrangement using the current density distribution, the magnet arrangement including a number of current carrying coils arranged within the magnet region.

5 Claims, 15 Drawing Sheets

(51) Int. Cl.
*G01R 33/38* (2006.01)
*G01R 33/3815* (2006.01)

(56) References Cited

U.S. PATENT DOCUMENTS

| | | | | |
|---|---|---|---|---|
| 5,677,630 | A * | 10/1997 | Laskaris et al. | 324/320 |
| 5,793,209 | A | 8/1998 | Kondo et al. | |
| 5,818,319 | A * | 10/1998 | Crozier et al. | 335/299 |
| 6,037,850 | A * | 3/2000 | Honmei et al. | 335/216 |
| 6,067,001 | A | 5/2000 | Xu et al. | |
| 6,084,497 | A * | 7/2000 | Crozier et al. | 335/299 |
| 6,218,923 | B1 * | 4/2001 | Laskaris et al. | 335/299 |
| 6,489,872 | B1 * | 12/2002 | Fukushima et al. | 335/299 |
| 6,507,259 | B2 * | 1/2003 | Westphal et al. | 335/301 |
| 6,580,346 | B1 * | 6/2003 | Takeshima et al. | 335/216 |
| 6,633,215 | B2 * | 10/2003 | Xu et al. | 335/216 |
| 6,680,612 | B1 | 1/2004 | McKinnon et al. | |
| 6,828,892 | B1 * | 12/2004 | Fukushima et al. | 335/299 |
| 6,853,281 | B1 * | 2/2005 | Kakugawa et al. | 335/296 |
| 6,947,877 | B2 | 9/2005 | Jensen | |
| 6,950,001 | B2 * | 9/2005 | Kruip et al. | 335/296 |
| 6,982,552 | B2 | 1/2006 | Hardy et al. | |
| 7,167,004 | B1 * | 1/2007 | Kruip | 324/320 |
| 7,479,860 | B2 * | 1/2009 | McDougall et al. | 335/299 |
| 7,791,340 | B2 * | 9/2010 | Heid | 324/307 |
| 7,898,258 | B2 * | 3/2011 | Neuberth et al. | 324/320 |
| 7,960,710 | B2 * | 6/2011 | Kruip et al. | 250/492.3 |
| 8,134,433 | B2 * | 3/2012 | Abe et al. | 335/216 |
| 8,154,368 | B2 * | 4/2012 | Westphal et al. | 335/216 |
| 8,222,985 | B2 * | 7/2012 | Neuberth et al. | 335/301 |
| 8,421,463 | B2 * | 4/2013 | Crozier et al. | 324/319 |

OTHER PUBLICATIONS

International Preliminary Report on Patentability (IPRP) (Chapter I) for PCT/AU2009/000572, mailed Nov. 9, 2010.
Tieng, Quang M., et al., "Globally optimal superconducting magnets Part I: Minimum stored energy (MSE) current density map," Journal of Magnetic Resonance, vol. 196, 2009, pp. 1-6.
Extended European Search Report dated Dec. 6, 2011, issued in European Patent Application No. 09741593.

* cited by examiner

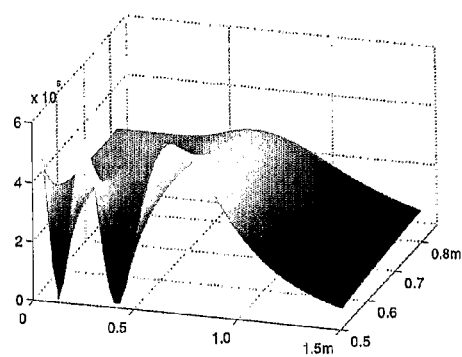 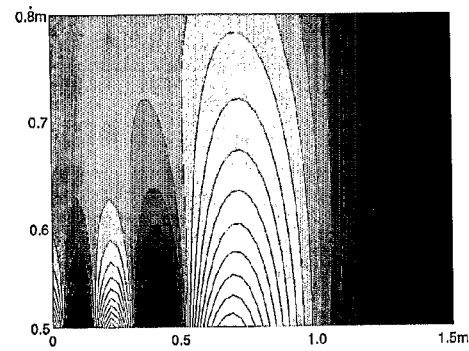
Fig. 8A                    Fig. 8B
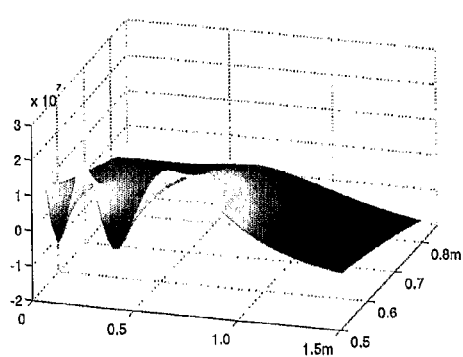 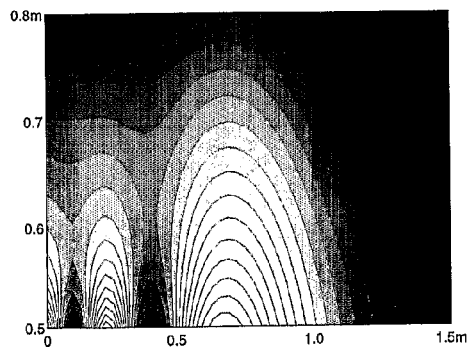
Fig. 9A                    Fig. 9B

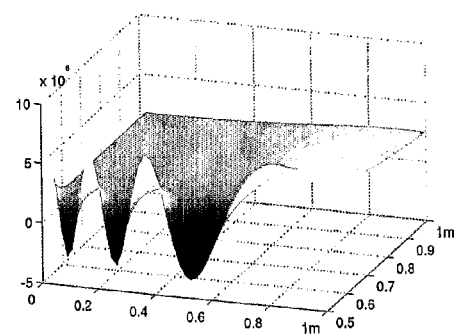 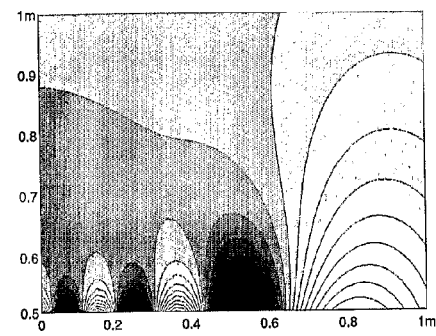
Fig. 10A                  Fig. 10B
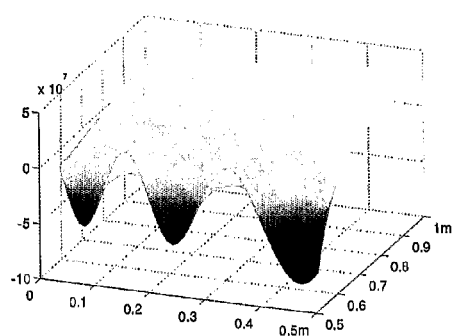 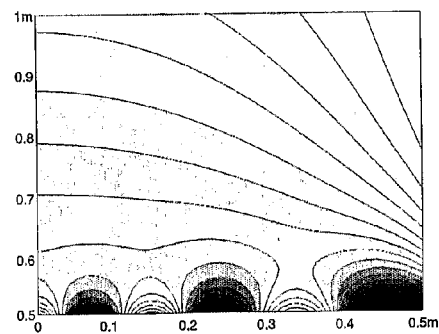
Fig. 11A                  Fig. 11B

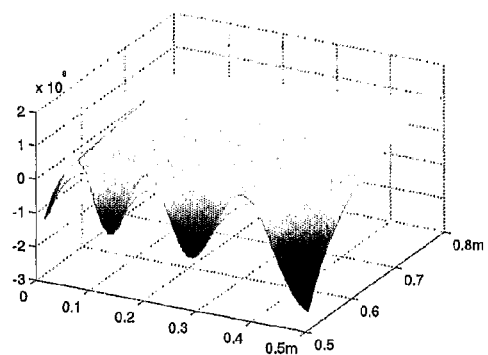 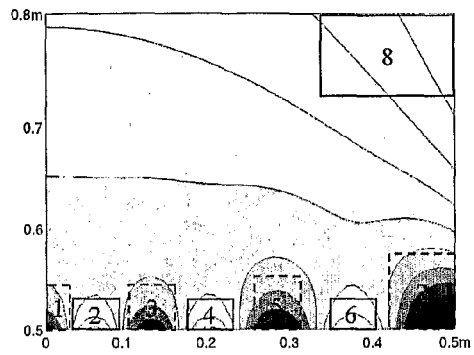
Fig. 14A                Fig. 14B
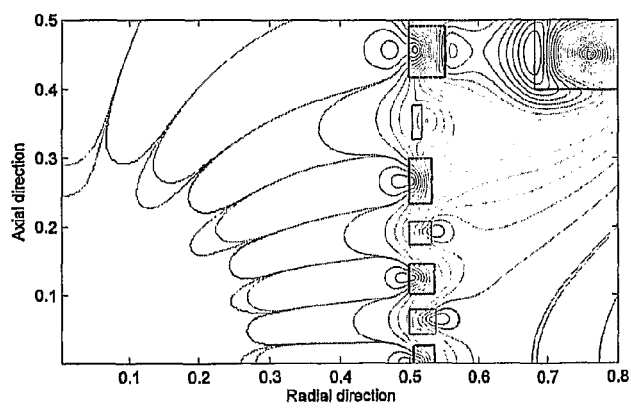 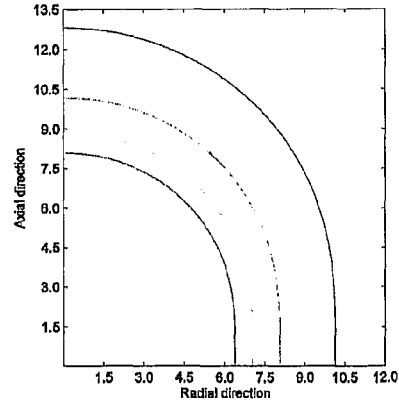
Fig. 15A                Fig. 15B

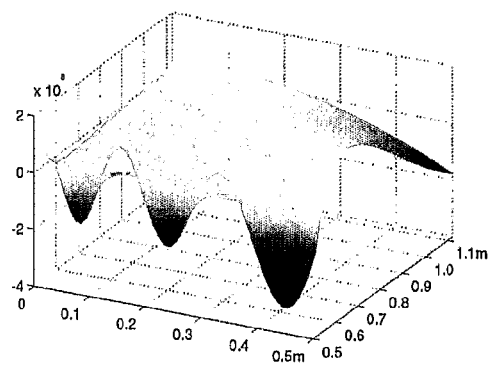 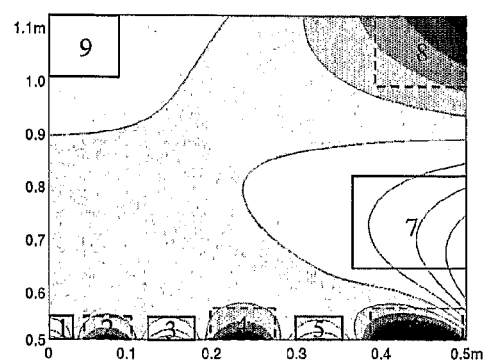
Fig. 16A     Fig. 16B
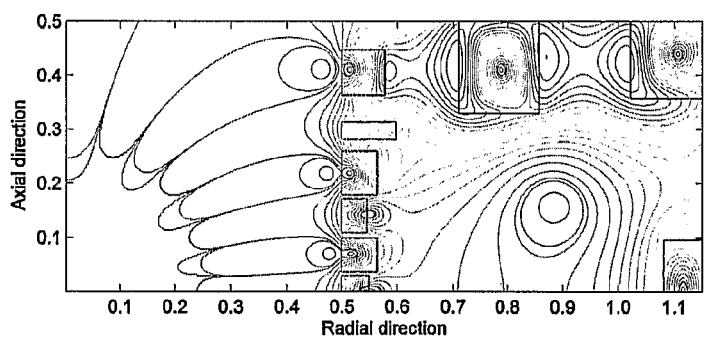 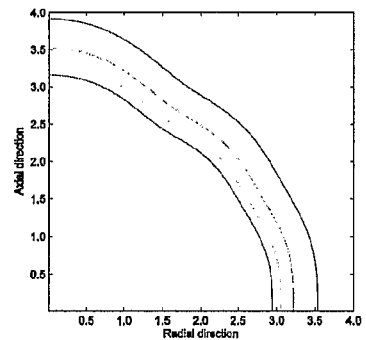
Fig. 17A     Fig. 17B

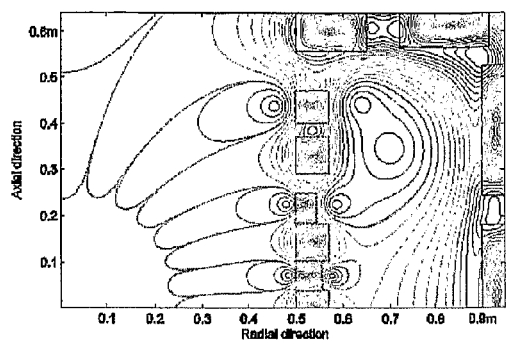 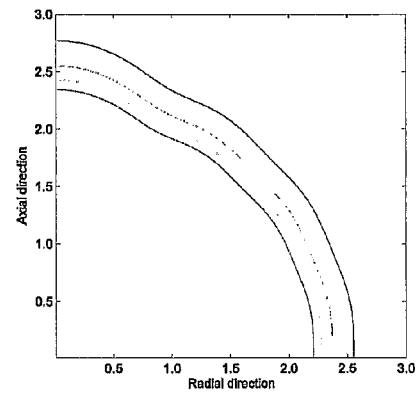
Fig. 18A　　　　　　　Fig. 18B
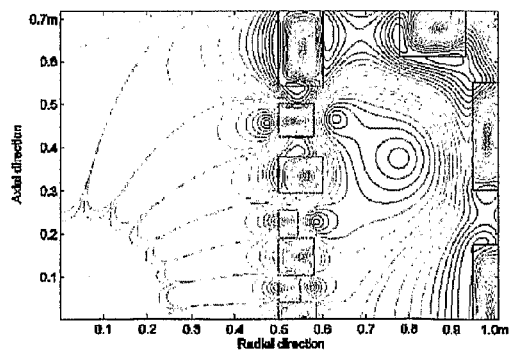 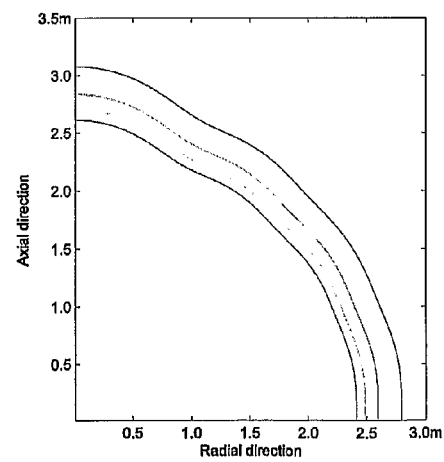
Fig. 19A　　　　　　　Fig. 19B

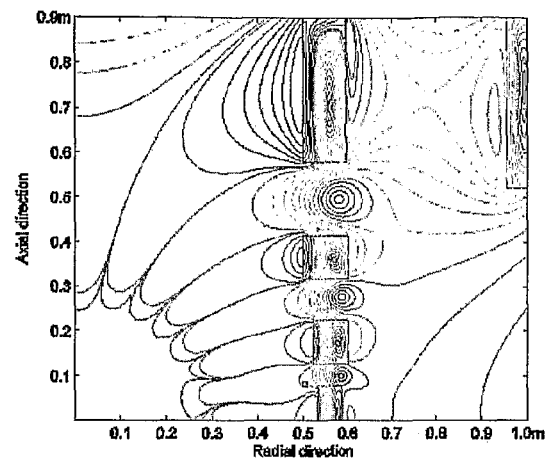 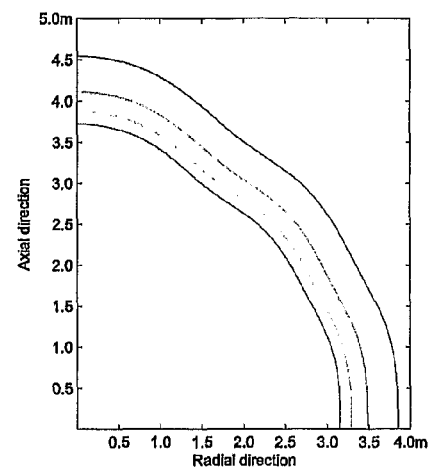
Fig. 20A                Fig. 20B
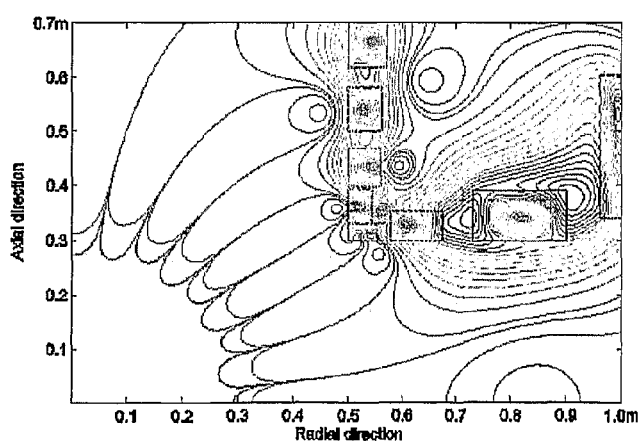 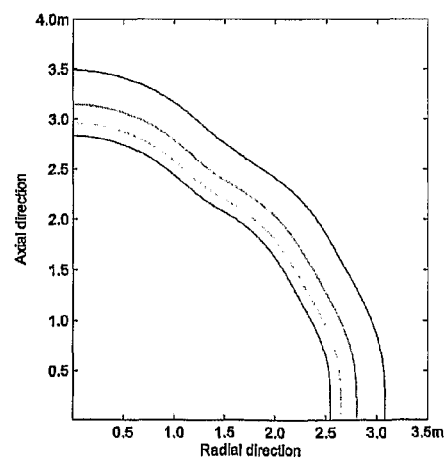
Fig. 21A                Fig. 21B

ARRANGEMENT OF COILS FOR MRI APPARATUS

This application is the U.S. national phase of International Application No. PCT/AU2009/000572, filed 7 May 2009, which designated the U.S. and claims priority to Australian Application No. 2008902243, filed 8 May 2008, the entire contents of each of which are hereby incorporated by reference.

BACKGROUND OF THE INVENTION

The present invention relates to a magnet arrangement and a method of determining a magnet arrangement, and in particular, a magnet arrangement for use in MRI (magnetic resonance imaging) or other similar applications.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The design of superconducting magnets has been widely investigated in the past using different optimization strategies to obtain coil layouts that have certain magnetic field properties.

Typically one desirable characteristic of an MRI magnet system is the ability to generate a strong and homogenous axial magnetic field over an imaging region, which is commonly referred to as the diameter sensitive volume (DSV). It is also desirable to restrict the peak magnetic field produced inside the superconductors themselves, and minimize the stray field external to the assembly.

The minimization of stray fields is a process generally referred to as shielding, and is historically achieved by placing coils as part of the assembly on the exteriors of the field producing magnet, to essentially reduce the stray field of the magnet and to minimize the size of the fringe field. Usually, active shielding is a process whereby coils with reverse current directions are placed on top of the main winding to reduce stray magnetic fields exterior to the magnet chamber.

Other factors that influence the design and manufacturing of magnets are related to geometrical constraints, that is, to reduce the magnet size, weight and associated wire cost, and the time taken to wind the individual coils that collectively comprise a magnet.

Previously investigated optimization methods to design superconducting magnets typically fall into two categories. The first involves searching a broad parameter space for an optimal coil layout, as described for example in Shaw, N. R. and R. E. Ansorge, *Genetic algorithms for MRI magnet design*. IEEE Transactions on Applied Superconductivity, 2002. 12: p. 733-736. The second places initial constraints on the optimization strategy to enable the attainment of a solution in either less time, or in a more convergent and stable manner, as described for example in Cheng, Y. C. N., et al., *Design of actively shielded main magnets: An improved functional method*. Magn. Res. Mat. Phys. Bio. Med., 2003. 16(2): p. 57-67.

The former technique tends to be associated with optimization strategies that require large computational resources, and the latter tends to achieve magnet coil layouts faster, given a good initial coil layout approximation or seed data. However, as described in Cheng, Y. C. N., et al., *A Comparison of Two Design Methods for MRI Magnets*. IEEE Transactions on Applied Superconductivity, 2004. 14(3): p. 2008-2014, both optimization categories tend to provide very similar results, irrespective of the search space.

US2005/0146332 describes a magnetic field generator for producing a homogenous magnetic field region and a method of designing an MRI system that produces a low fringe field region. The method comprises defining a solution space, defining a field of view, a centre field and homogeneity requirements, defining fringe field requirements, and running an optimization algorithm to determine coil positions. However, the optimisation algorithm does not yield a single global optimum solution, and consequently leads to localised minima, making the determination of an optimum layout complex.

U.S. Pat. No. 6,255,929 describes a method of making optimized electromagnets. Whilst the described technique allows the magnet design optimization problem to be cast as an L1-norm minimization linear programming calculation, for which a global solution can always be found, limitations still exist.

In one example, the magnets are optimized to require the least amount of dissipated power for the given predetermined axial magnetic field, which can only be used for resistive and not superconducting magnets. In another example, superconducting magnet designs are produced by minimising the length of superconducting wire used. Thus, different analysis is required for superconducting and resistive magnets.

The minimisation process is based on a constant current density coil configuration, which does not necessarily result in an optimum magnet design. Furthermore, the global solution arises from casting the problem as a simpler L1-norm minimisation calculation allowing a global solution within the constrains of the specified functions and does not therefore represent a optimum magnet configuration.

The approach also employs a virtual coil comprising an infinitesimally thin conductor. Each iteration of the design process requires an update of the virtual coil, which makes the process inappropriate for superconducting coil design. This is highlighted by the fact that the method only caters for unshielded long magnets in which each of the coils are wound in the positive sense.

U.S. Pat. No. 5,760,582 describes gradient coil assemblies and shim coil assemblies for magnetic resonance imaging ("MRI") devices, wherein the coil assemblies comprise a coil support and a conductive wire having a locus described by a solution of a current continuity equation over a finite interval for which certain terms of the magnetic field expansion are equal to zero, to generate non-uniform magnetic fields. The gradient coil produces gradient magnetic fields and linear magnetic fields which cancel non-uniformities in the magnetic field of the magnet of the MRI device. Shim coils can be used to cancel such non-uniformities, as well.

It will be appreciated that as these techniques are described for use in gradient and shim coil assemblies, these would not be considered as suitable for use in designing a primary magnet arrangement.

U.S. Pat. No. 5,382,904 describes superconducting electromagnets suitable for use in the NMR tomography of human organs. Each of the disclosed electromagnets are constructed according to a methodology for structured coils, where the desired field at locations within the volume of interest and, optionally, outside of the location of the coils is selected; the current magnitude and polarity for a plurality of coil element locations are then optimized, by way of a computer program, to provide the desired field magnitude at the locations. The magnet construction results in a plurality of coils of varying current polarity, and of irregular shape and size, optimized to provide the uniform field within the DSV. However, the irregular coil shapes are difficult to produce in practice, thereby limiting the applicability of this technique.

U.S. Pat. No. 5,818,319 describes procedures for designing magnets, including superconducting magnets, shim magnets, and gradient magnets for magnetic resonance systems. The to procedures involve the use of a simulated annealing procedure in which weighted spherical harmonics are included in the procedure's error function. The procedure has resulted in the development of previously unknown magnet designs. In particular, superconducting magnets have been designed that include at least one coil in which the current flow is opposite to that in adjoining coils. Such reversed flow in combination with a relatively large number of coils, e.g., more than 6 coils, have enabled the development of short, yet homogeneous, whole body magnets for use in magnetic resonance imaging (MRI).

However, such magnet systems, and methods of designing the magnet systems still include some limitations. For example, the use of simulated annealing processes is computationally expensive. Furthermore, the minimization function used in the simulated annealing process has multiple local minima, meaning that when a minima is found, there is no guarantee that this is the optimum, or the global solution. Consequently, using these techniques can result in non-optimal magnet designs.

SUMMARY OF THE PRESENT INVENTION

It is an object of the present invention to substantially overcome, or at least ameliorate, one or more disadvantages of existing arrangements.

In a first broad form the present invention provides a method of determining a magnet arrangement for use in magnetic resonance imaging apparatus, the method including:
  a) determining a function representing current densities required within a magnet region to generate a field;
  b) determining a current density distribution required to generate a desired field, using the function; and,
  c) determining the magnet arrangement using the current density distribution, the magnet arrangement including a number of current carrying coils arranged within the magnet region.

Typically the method includes:
  a) dividing the magnet region into a number of elements; and,
  b) determining a current density for each element using the function to thereby determine the current density distribution.

Typically the method includes determining the current density distribution by optimizing the function.

Typically the function has a global minimum.

Typically the function is quadratic with respect to the current density within the magnet region.

Typically the function is based on the energy stored within the magnet region.

Typically the function is of the form:

$$F \propto LI^2$$

where:
  (a) F is the cost function;
  (b) I is the current density within the magnet region; and
  (c) L is related to an inductance.

Typically the method includes defining the magnet region.

Typically the magnet region has an arbitrary shape positioned relative to at least one of:
  a) a bore; and,
  b) an imaging region.

Typically the magnet region substantially surrounds at least one of:
  a) a bore; and,
  b) an imaging region.

Typically the magnet region is rotationally symmetric with respect to a field axis.

Typically the field axis is aligned with a bore axis.

Typically magnet region has a substantially cylindrical shape.

Typically the method includes, defining a desired field within at least one of:
  a) an imaging region; and,
  b) a stray field region.

Typically the method includes defining the imaging region to have a substantially predefined shape positioned with respect to the magnet region.

Typically the method includes defining an imaging region having a substantially spherical shape positioned on a field axis radially inwardly of the magnet region.

Typically the method includes defining a desired field including a substantially homogeneous magnetic field within an imaging region.

Typically the desired field has a homogeneity having a variation in the imaging region of less than at least one of:
  a) 100 ppm;
  b) 20 ppm; and,
  c) 10 ppm.

Typically the method includes defining a stray field region substantially surrounding the magnet region.

Typically the stray field region is positioned on the bore axis radially outwardly of the magnet region.

Typically the method includes defining a desired field including a field strength of less than a selected amount within the stray field region.

Typically the selected amount is less than, at least one of:
  a) 20 Gauss;
  b) 10 Gauss; and,
  c) 5 Gauss.

Typically a current density distribution has a series of extremities lying around a perimeter of the magnet region.

Typically the direction of current flow in the coils depends on the polarity of the extremities within the current density distribution.

Typically the method includes using the current density distribution to determine at least one of:
  a) coil locations within the magnet region;
  b) coil sizes;
  c) a current density within coils;
  d) a total current for coils;
  e) current flow directions within coils; and,
  f) coil winding directions.

Typically the method includes determining the coil arrangement based on extremities within the current density distribution.

Typically the coils are located on local positive maxima and local negative minima of the current density distribution.

Typically the current carrying coils are arranged substantially around a perimeter of the magnet region.

Typically, for current carrying coils on a bore perimeter of the magnet region, each current carrying coil carries a current in an opposing direction to each adjacent coil.

Typically each current carrying coil carries a current in an opposing direction to each adjacent coil.

Typically the magnet region has a substantially cylindrical shape surrounding a field axis, each current carrying coil being arranged within the magnet region with a coil axis substantially aligned with the field axis.

Typically the method further includes optimising the coil arrangement.

Typically the method includes:
a) defining a second function; and,
b) optimising the second function to thereby optimise the coil arrangement.

Typically the method includes optimising the second function such that the coil arrangement has optimal coil current densities Typically the second function has a global solution.

Typically the second function is quadratic with respect to the current density within the magnet region.

Typically the second function is a function of the energy stored within the coils.

Typically the method includes:
a) defining coil constraints; and,
b) optimising the second function using the coil constraints to thereby determine an optimised magnet arrangement.

Typically the coil constraints include at least one of:
a) a minimum separation between coils to prevent coil overlap; and,
b) an optimal current density flow for each coil.

Typically the optimal current density flow is smaller than a maximum current density.

Typically method includes selecting the maximum current density in accordance with a magnetic field strength and properties of superconducting material used in the current carrying coils.

Typically the method is performed at least in part using a processing system.

In a second broad form the present invention provides a magnet arrangement for use in magnetic resonance imaging apparatus, the magnet arrangement including a number of current carrying coils arranged substantially around a perimeter of a magnet region, and wherein, for current carrying coils on a bore perimeter of the magnet region, each current carrying coil carries a current in an opposing direction to each adjacent coil on the bore perimeter.

Typically the current carrying coils are located substantially on extremities of a current density distribution determined for the magnet region.

Typically each coil carries a current in a direction defined by a polarity of the extremity.

Typically each coil carries a current in an opposing direction to each adjacent coil.

Typically each coil includes a number of current carrying windings.

Typically the number of current carrying windings is determined so that the coil generates a required magnetic field.

Typically the magnet region has an arbitrary shape positioned relative to at least one of:
a) a bore; and,
b) an imaging region.

Typically the magnet region is rotationally symmetric with respect to a field axis.

Typically the field axis is aligned with a bore axis.

Typically magnet region has a substantially cylindrical shape.

Typically the magnet generates a desired field within at least one of:
a) an imaging region; and,
b) a stray field region.

Typically the imaging region has a substantially predefined shape positioned with respect to the magnet region.

Typically the imaging region has a substantially spherical shape positioned on a field axis radially inwardly of the magnet region.

Typically the imaging region has a substantially homogeneous magnetic field.

Typically the homogeneity has a variation of less than at least one of:
a) 100 ppm;
b) 20 ppm; and,
c) 10 ppm.

Typically the stray field region substantially surrounds the magnet region.

Typically the stray field region is positioned on the field axis radially outwardly of the magnet region.

Typically the desired field has a field strength of less than a selected amount within the stray field region.

Typically the selected amount is less than, at least one of:
a) 20 Gauss;
b) 10 Gauss; and,
c) 5 Gauss.

BRIEF DESCRIPTION OF THE DRAWINGS

An example of the present invention will now be described with reference to the accompanying drawings, in which:—

FIGS. 8A and 8B are 3D and 2D representations of examples of minimum stored energy (MSE) current density profiles for 3 m long magnet domains for unshielded order 10 degree 0 configurations;

FIGS. 9A and 9B are 3D and 2D representations of examples of MSE current density profiles for 3 m long magnet domains for shielded order 10 degree 2 configurations;

FIGS. 10A and 10B are 3D and 2D representations of examples of MSE current density profiles for unshielded order 14 degree 0 2 m length magnet configurations;

FIGS. 11A and 11B are 3D and 2D representations of examples of MSE current density profiles for unshielded order 14 degree 0 1 m length magnet configurations;

FIGS. 14A and 14B are 3D and 2D representations of examples of MSE current density profiles for unshielded order 16 degree 0 1 m length magnet configurations;

FIGS. 15A and 15B are representation of the resulting DSV magnetic field with final coil arrangement and stray fields for the initial magnet configuration of FIG. 14B;

FIGS. 16A and 16B are 3D and 2D representations of examples of MSE current density profiles for shielded order 14 degree 4 1 m length magnet configurations;

FIGS. 17A and 17B are representations of the resulting DSV magnetic field with final coil arrangement and stray fields for the initial magnet configuration of FIG. 16B;

FIGS. 18A and 18B are representations of the resulting DSV magnetic field with final coil arrangement and stray fields for a short bore clinical magnet;

FIGS. 19A and 19B are representations of the resulting DSV magnetic field with final coil arrangement and stray fields for a short bore 3.0T clinical magnet;

FIGS. 20A and 20B are representations of the resulting DSV magnetic field with final coil arrangement and stray fields for a high field clinical magnet; and, FIGS. 21A and 21B are representations of the resulting DSV magnetic field with final coil arrangement and stray fields for an open bore clinical magnet.

DETAILED DESCRIPTION OF THE PREFERRED EMBODIMENTS

Figure 1:
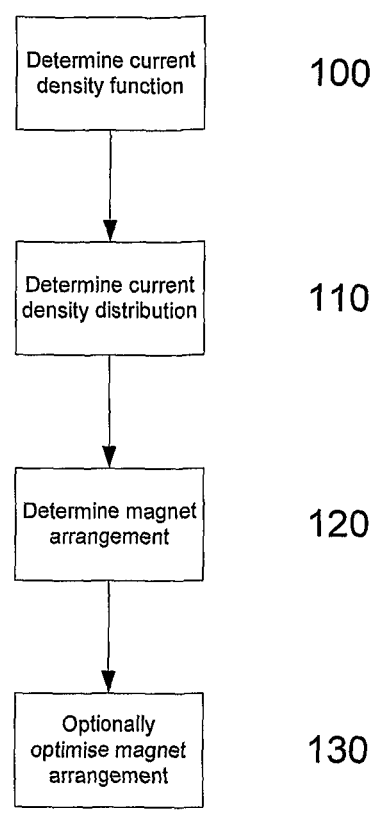
FIG. 1 is a flow chart of an example of a process for determining a magnet arrangement.

An example of a process for designing a magnet arrangement for use in MRI or other similar applications will now be described with reference to FIG. 1.

In this example, at step 100, a function is determined representing the current densities required within a magnet region in order to generate a given field.

The nature of the function may vary depending on the preferred implementation and an example function will be described in more detail below. However, in one example, the function is based on the stored energy within the magnet coils, and hence can be quadratic with respect to the current density, when combined with a term representing a coil inductance. The use of a function that is quadratic with respect to the current density means that the function has a single global solution for a given desired field.

At step 110 a current density distribution required in order to generate a desired field is determined using the function.

The desired field may be any suitable field required for performing MRI, and will typically therefore require the presence of a suitably homogenous field in an imaging region, and a low external stray field magnitude. The desired field will therefore depend on factors such as the nature of the MRI process being performed. The current density is typically determined in any one of a number of ways depending on the nature of the function used, but in one example, this involves finding a minimum or maximum of the function for the desired field, as will be described in more detail below.

In one example, the resulting current density distribution has a series of extremities lying around the perimeter of the magnet region. For larger magnet regions, the current density may have a relatively large number of maxima and minima of a common polarity, so that for example, positive maxima are adjacent to positive minima, or vice versa. As the size of the magnet region is reduced, the number of such extremities becomes smaller, with a further reduction in size resulting in the adjacent extremities having opposite polarities, such that positive maxima are located adjacent to negative minima.

Once a current density distribution within the magnet region has been determined, this can be used to determine the magnet arrangement at step 120.

The magnet arrangement will typically specify one or more magnet parameters, such as a number and location of current carrying coils within the magnet region, the respective current density and/or total current required for each coil, the direction of current flow within the coils, or the like. In one example, the arrangement is at least partially based on the location and/or magnitude of extremities, such as local positive maxima and local negative minima, in the ideal current density distribution obtained for the specified magnet parameters.

At step 130 the magnet arrangement determined in step 120 can be optimised further, using an optimisation strategy.

This can be performed in any suitable manner, and may be used to refine the magnet arrangement, for example to ensure that the current density for each current carrying coil is feasible, and to ensure the peak field on the coil is within acceptable ranges.

Figure 2A:
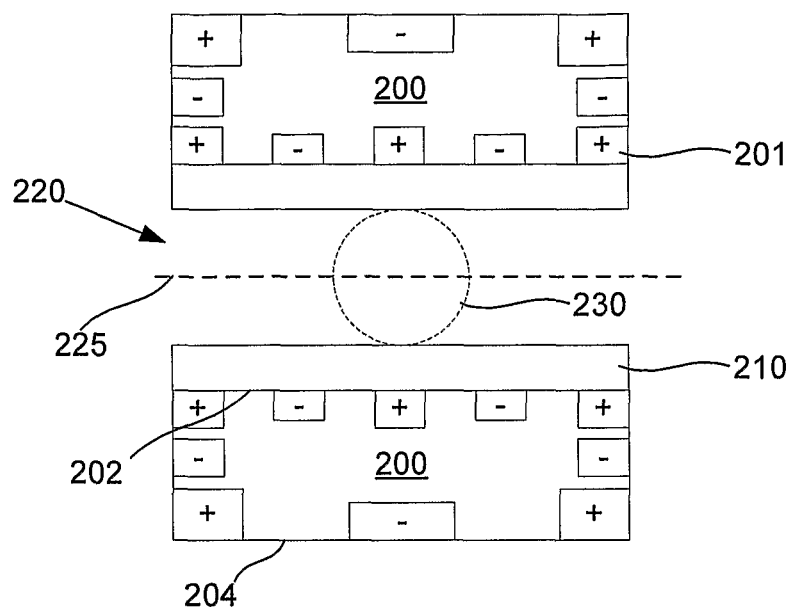
FIG. 2A is a schematic side view of an example magnet arrangement generated using the process of FIG. 1.
Figure 2B:
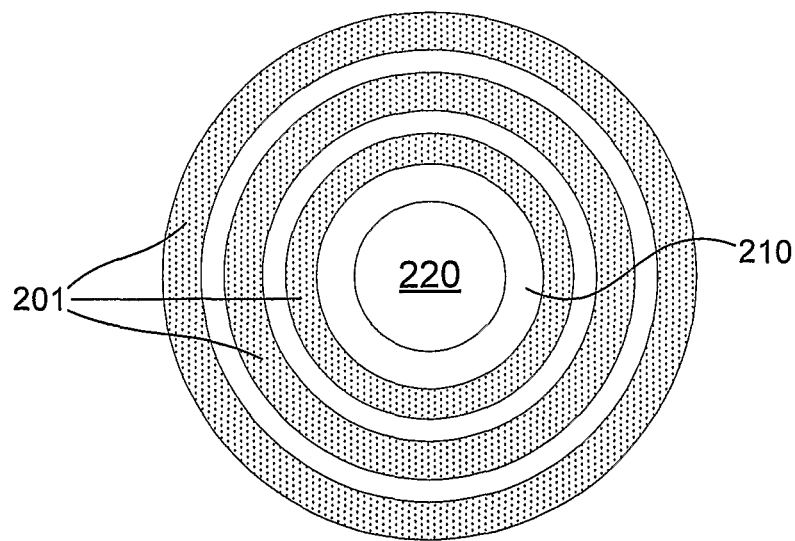
FIG. 2B is a schematic end view of the magnet arrangement of FIG. 2A.

An example of a coil arrangement determined utilising the above described methodology will now be described in more detail with reference to FIGS. 2A and 2B.

In this example, a cylindrical magnet region 200 is provided surrounding a cylindrical bore 220, defining a bore axis 225. The magnet region 200 contains a number of current carrying coils 201, having their axes aligned with the bore axis 225, which are used to generate a desired magnetic field within an imaging region 230. This configuration results in a magnetic field that is rotationally symmetric about a magnetic field axis (not shown) that is aligned with the bore axis 225. A coil region 210 is also typically provided between the magnet region 200 and the bore 220 for containing RF coils, shim coils and/or gradient coils, as required for the respective MRI process.

In this example, the coils 201 are generally spaced apart around the perimeter of a magnet region 200, which results from performing the methodology described above. Furthermore, the number, size and shape of the coils is not intended to be limiting and is merely for illustrative purposes, as will become apparent from the specific examples described in more detail below.

The direction of current flow in each of the coils is indicated by the "+" and "−" symbols, showing that in at least some of the resulting magnet arrangements, the current flow in each adjacent coil is in an opposite direction to that in each other adjacent coil. This is not essential, and arrangements with current flows in adjacent coils in the same direction are described. However, in general the opposing current flow arrangement results in a more optimal and compact design.

Accordingly, current flow in at least the coils along a bore perimeter boundary 202 adjacent the bore 220 are typically in opposing directions. For optimum performance current flow in each coil is opposite the current flow in each adjacent coil for the entire perimeter. Current flow in opposing directions may be achieved in any one of a number of ways, such as by reverse winding adjacent coils, or by controlling the current flow in each coil.

The magnet arrangement described above, and in particular, the positioning of coils around the perimeter of the magnet region, and the reverse current directions for adjacent coils results in a significantly improved field generating capability. In particular, for an imaging region of a given homogeneity and size, this can generally be produced by a magnet arrangement having a shorter axial length than can be achieved using prior art techniques and arrangements. Furthermore, the arrangement typically results in improved homogeneity within the imaging region, and a reduction in stray field (or fringe field) levels outside the magnet region.

It will therefore be appreciated that this represents a significant improvement over prior art magnet arrangements, and magnet arrangement protocols.

Figure 2C:
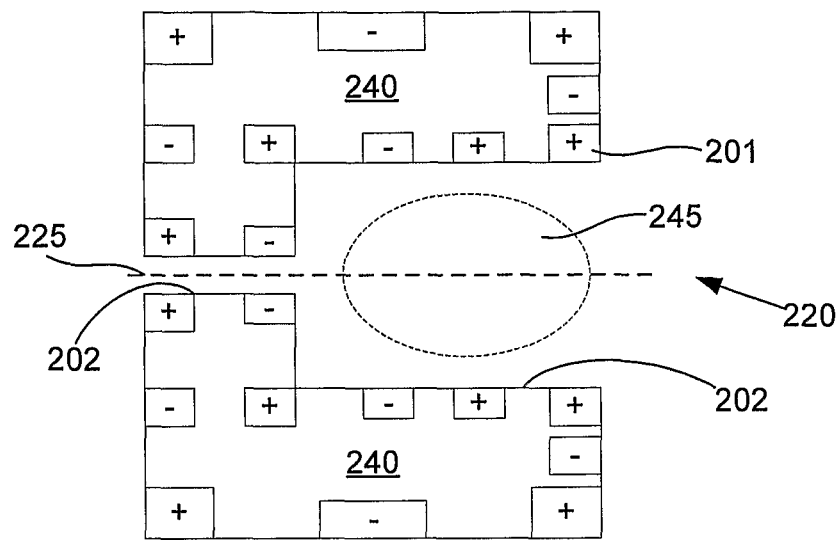
FIG. 2C is a schematic side view of a second example magnet arrangement generated using the process of FIG. 1.
Figure 2D:
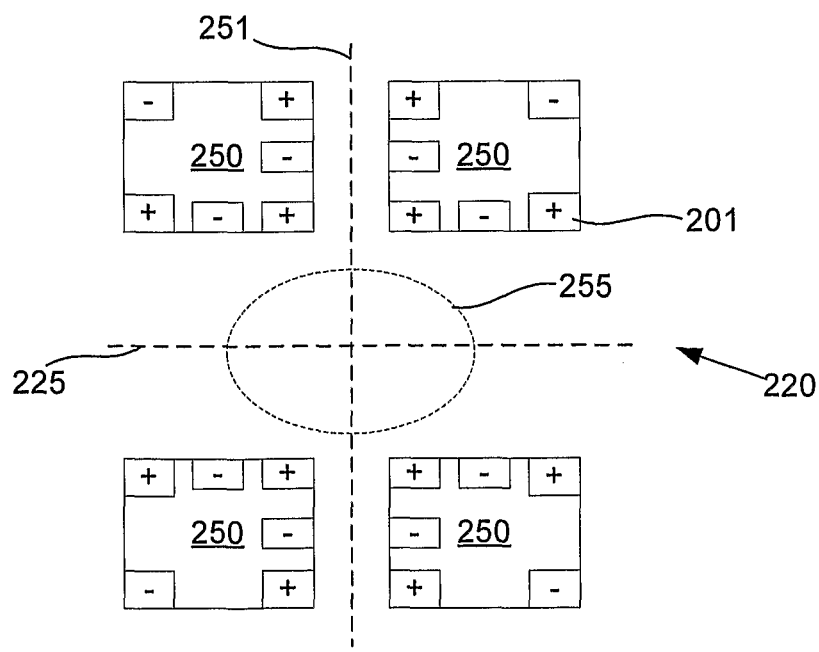
FIG. 2D is a schematic side view of a third example magnet arrangement generated using the process of FIG. 1.
Figure 2E:
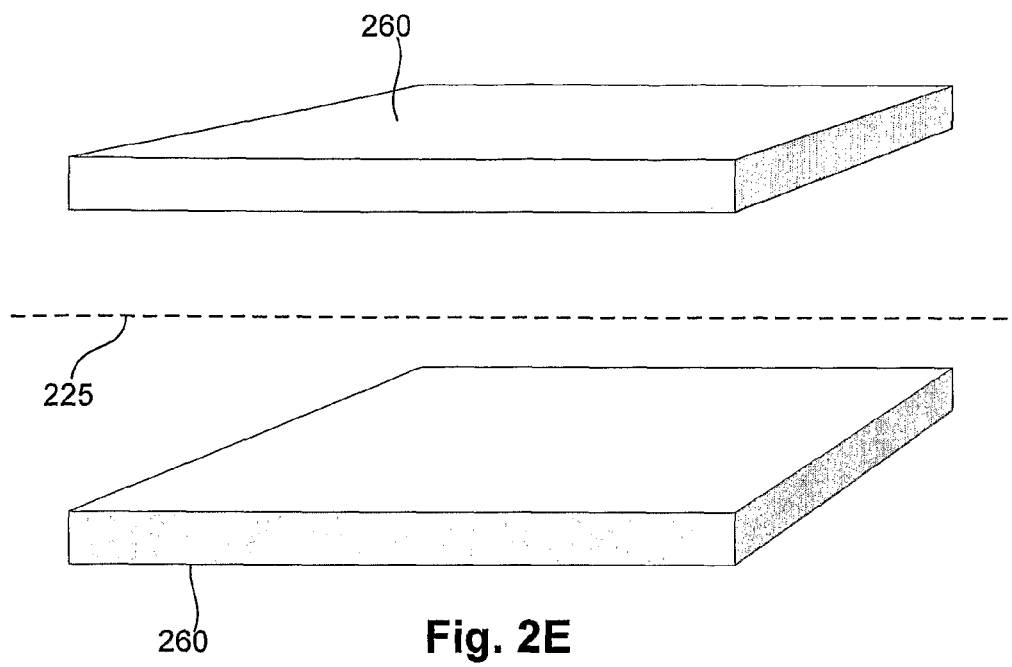
FIG. 2E is a schematic perspective view of a fourth example magnet arrangement generated using the process of FIG. 1.

The techniques can also be applied to a wide range of different magnet region configurations, examples of which are shown in FIGS. 2C, 2D and 2E.

In the example of FIG. 2C, an alternative design of magnet region 240 is provided. In this example, the magnet region 240 is still rotationally symmetrical about the bore axis 225, but has a non-rectangular cross section, resulting in a non-circular imaging region 245. It is apparent from this, that a magnet region having any desired cross sectional shape can be used.

In the example of FIG. 2D, a further alternative design of magnet region 250 is provided. In this example, the magnet region 250 is rotationally symmetrical about a field axis 251, which is substantially perpendicular to the bore axis 225. It is apparent from this, that the field axis 251 need not be coincident with the bore axis 225.

In the example of FIG. 2E, two magnet regions 260 are provided, situated on either side of an effective bore axis 225. In this example, the magnet region 260 is not rotationally symmetrical, but does define a field axis that is coincident with the effective bore axis 225.

It will be appreciated from the above, that virtually any configuration of magnet region can be defined. In one example, the magnet region has any arbitrary shape that is optionally rotationally symmetric with respect to a bore or field axis. However, this is not necessary and for example, non rotationally symmetric arrangement can be used. Additionally, whilst the magnet region surrounds the imaging region in the above examples, the imaging region can instead be offset from the magnet regions, as occurs for example in open magnet configurations.

Figure 3:
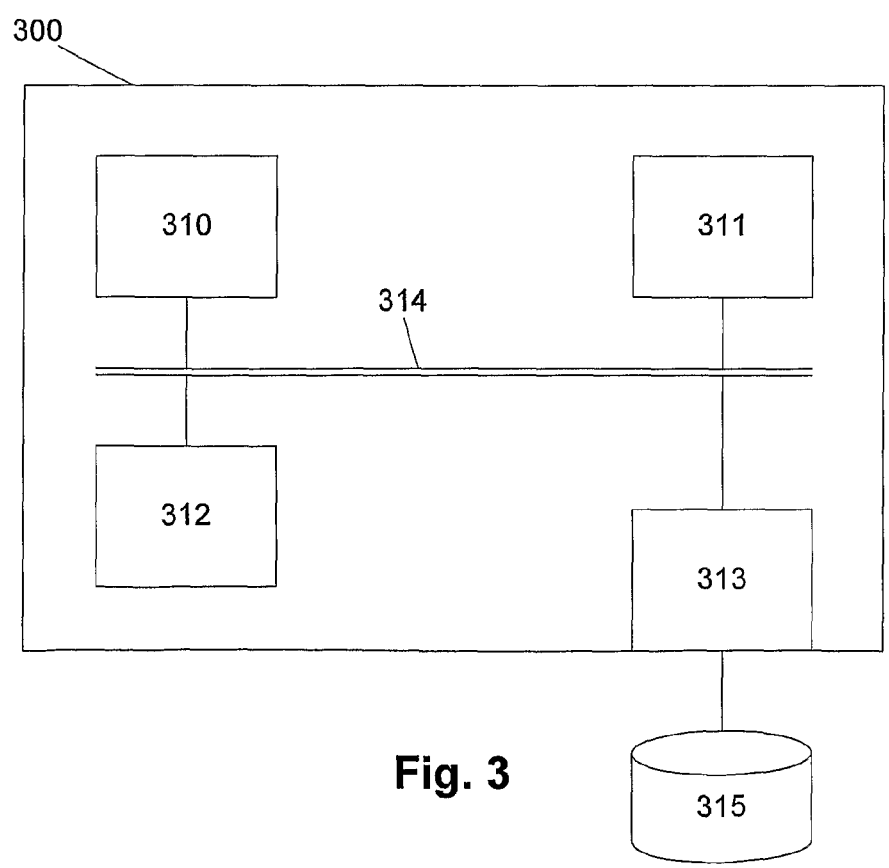
FIG. 3 is a schematic diagram of an example processing system.

In one example, the above described process is performed at least in part utilising a processing system, an example of which will now be described with reference to FIG. 3. In this example the processing system 300 includes a processor 310, a memory 311, an input/output device, such as a keyboard and mouse 312, and an optional external interface 313 coupled together via a bus 314. The optional external interface may be coupled to a database 315, allowing the processing system 300 to store data and/or access previously stored data.

In use, the processor 310 typically executes applications software stored in the memory 311, to allow the processor 310 to perform required calculations and/or display results. This can include, for example, performing analysis of the function and desired field in order to generate the current density distribution, displaying the current density distribution to a user, determining the magnet arrangement and performing further optimisation. It will be appreciated that these processes can be performed automatically, but typically involve at least some input or other control by the user.

It will therefore be appreciated that the processing system 300 may be a suitably programmed computer system, such as a laptop, desktop, PDA, computer server, or the like, although alternatively the processing system 300 may be formed from specialised hardware.

Figure 4A:
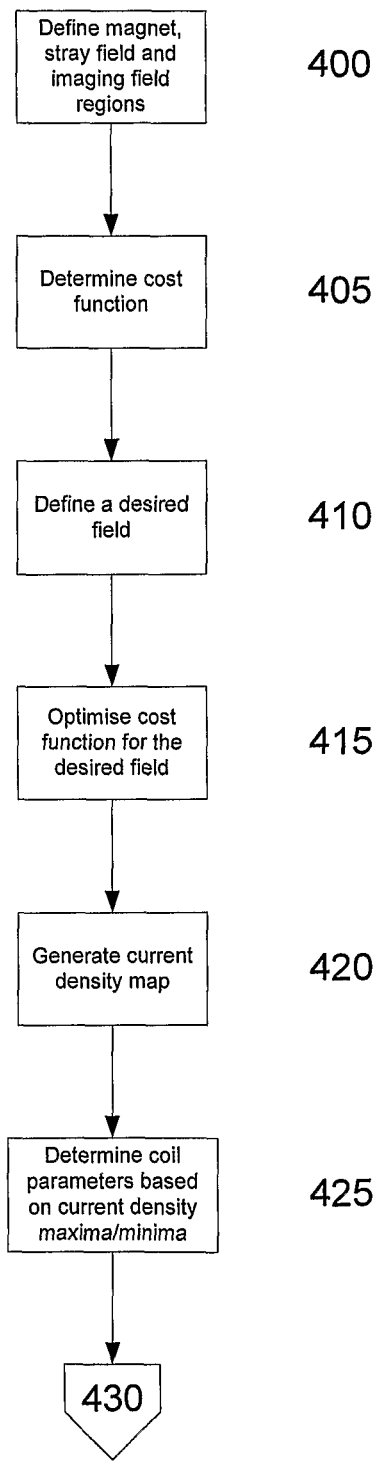
FIGS. 4A and 4B are a flow chart of a second example of a process for determining a magnet arrangement.
Figure 4B:
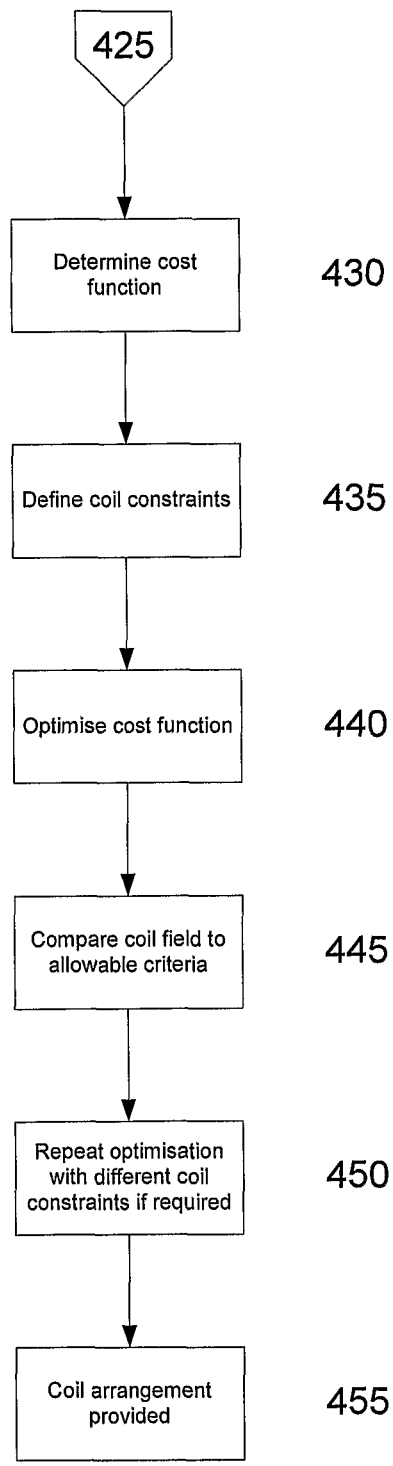

An example of the magnet design process will now be described in more detail with reference to FIGS. 4A and 4B.

In this example, at step 400 a magnet region, stray field region and imaging region are defined. The regions will typically be defined based on a combination of the MRI imaging requirements and the required physical size of the resulting arrangement. Thus, for example, the imaging region is typically defined based on the need to encompass a certain physical volume depending on required imaging purposes. It will be appreciated that a number of different standard configurations are known, such as short bore configuration or the like, and these can therefore be generated by appropriate configuration of the regions.

Defining the regions will typically be achieved by allowing the user to input parameters into the processing system 300 representing the respective regions. This may be achieved in any suitable manner and can include the use of a graphical user interface for displaying a representation of the defined field regions, or the like.

At step 405 a cost function is defined based on the current density within the magnet region. The cost function is typically proportional to the energy stored within the magnet region, which in turn depends on the current density and an inductance within the region. This leads to an equation of the form:

$$F \propto LI^2$$

where:
F is the cost function;
I is the current density within the magnet region; and
L is related to an inductance.

The inductance and current density are typically summed over finite elements defined throughout the magnet region, as will be described in more detail below. Accordingly, in this instance, the inductance corresponds to the inductance that a coil within the region may have and can include a self inductance and/or a mutual inductance.

By basing the cost function on the square of the current density, the function has a single global maximum or minimum (depending on whether the function is negative or positive), thereby leading to a single optimum configuration for a desired field. Furthermore, as the cost function is indicative of the energy stored in current carrying coils located within the magnet region, finding the minimum therefore minimises the total stored energy, which in turn minimises quenching strains and the amount of superconducting wire used in the design.

The cost function can be defined in a case-by-case basis, but in one example is pre-defined in applications software executed by the processing system 300.

At step 410, a desired field configuration is determined. The desired field is determined based on imaging field and stray field requirements, which will typically require that the magnetic field is substantially homogenous across the entire volume of the imaging region, and typically has homogeneity of at least 100 ppm, typically better than 20 ppm, and preferably better than 10 ppm. Similarly, the stray field typically needs to be minimised to avoid undue interference with equipment external to the magnet configuration, and therefore preferably has a strength below 20 Gauss, and preferably below 15, 10 or even 5 Gauss.

The field requirements can be defined manually by having a user input appropriate parameters. Additionally, and/or alternatively, appropriate parameters may be pre-defined in the applications software executed by the processing system 300.

At step 415, the cost function is optimised for the desired field based on the definitions provided in step 410. The manner in which the cost function is optimised will vary depending on the preferred implementation. However, as mentioned above, by using the above described form of cost function, this leads to a single global minima for a given desired field, which in turn allows a single solution to be derived. Accordingly, this allows the processing system 300 to perform appropriate calculations, allowing the minima to be determined.

At step 420 the processing system 300 generates a current density map which can then be optionally displayed to a user via the I/O device 312, using a suitable user interface. The current density map represents the current densities required within the magnet region in order to generate the desired field, and particular example current density maps will be described in more detail below.

At step 425 coil parameters are determined based on the current density distribution. This may be achieved in any one of a number of ways such as by manual definition by a user, or through automatic definition in the processing system 300. Thus, for example, the user can be presented with a representation of the current density map, allowing the user to indicate preferred coil parameters using the I/O device 312, such as a mouse.

The parameters determined can include any one or more of coil locations, coil sizes, coil shapes, current directions, coil winding directions, or the like. Coil locations are typically defined to correspond to the locations of extremities in the current density distribution, whilst coil sizes and shapes depend on magnitude of the extremities.

The coil winding direction then depends on whether the current density for a given maxima or minima is positive or negative. As discussed above, the coil winding direction may represent a physical direction for the coil winding or alternatively may represent a direction of current flow through the coil, depending on the preferred implementation.

At this stage, the coil arrangement represents an unoptimised coil layout. Accordingly, in one example, further optimisation may be performed.

In this example, at step 430 a second cost function is determined. This is typically of a similar form to the cost function described above, and a specific example will be described in more detail below. Again, the cost function can be pre-defined in the applications software executed by the processing system 300.

At step 435 coil constraints are defined. The coil constraints will typically include limitations such as providing at least a minimum separation between coils to prevent coil overlap, as well as providing a maximum current density flow for each coil. These represent physical constraints on coils which are practically implementable, and are typically selected based on a required magnetic field strength and properties of superconducting material used in the current carrying coils.

At step 440 the coil layout cost function can be optimised to allow an optimised coil configuration to be determined. The optimisation is typically performed using quadratic sub-problems given constraints, as will be described in more detail below, although any suitable technique may be used.

It will be appreciated that in this instance, instead of optimising for current density throughout the magnet region, the optimisation is performed specifically with respect to the coils and their current densities, thereby differing from the previous optimisation problem.

At step 445 the obtained coil parameters for each coil are then compared to allowable criteria to ensure that the coil location and peak field constraints are met. Thus, for example, this can include ensuring the coils do not overlap, and that the maximum peak field on the coil is within an acceptable range. The optimisation can be repeated with different coil constraints, if this is required at step 450. Otherwise, the resulting coil arrangement can be provided as an output by the processing system 300 at step 455.

A specific example will now be described in more detail.

For the purpose of this example, the magnetic field produced by an arbitrarily shaped electric current carrying conductor is expressed as the sum of an infinite series of spherical harmonics. The amplitude and sign of each spherical harmonic expansion term depends on the coil geometry, current strength, winding direction and relative positions of coils in a particular magnet configuration.

A collective set of coils can be organised in space to meet the needs of a specific application by appropriate choice of size, current magnitude and direction, and spacing, to emphasise certain spherical harmonic expansion terms that define the magnetic field produced by the current carrying coils themselves.

Figure 5:
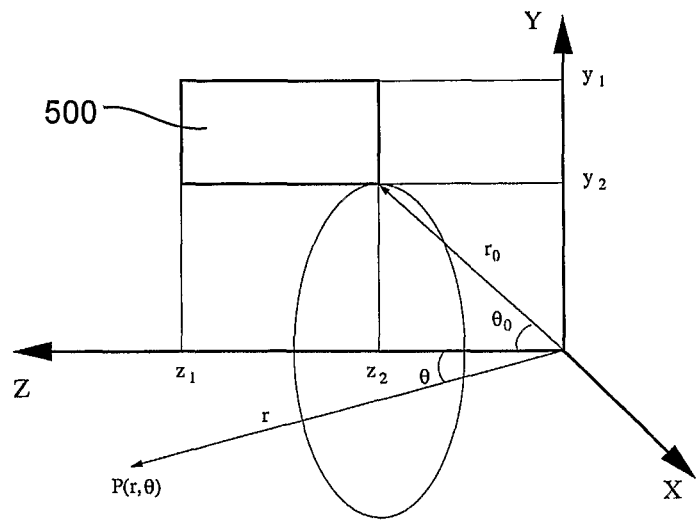
FIG. 5 is a schematic representation of a coordinate system used in determining a magnet arrangement.

An example of the geometry and reference frame for a cylindrical coil in space is shown in FIG. 5, which defines the magnetic field at point $P(r,\theta)$ produced by a superconducting coil, having cross section 500 located in the illustrated yz-plane. For the purpose of this example, appropriate symmetry is assumed to characterize the cylindrical nature of the problem, and the problem is simplified to 2D due to the inherent symmetry.

The axial component of the magnetic field at a point $(r<r_0, \theta)$ in an axisymmetric configuration comprising current carrying circular filaments coaxial with the z-axis is given by:

$$B_z(r < r_0, \theta) = I \sum_{n=1}^{\infty} a_n P_{n-1}(\cos\theta) r^{n-1}, \quad (1)$$

where $$a_n = -\frac{\mu_0}{2} \sin\theta_0 \frac{P_n^1(\cos\theta_0)}{r_0^n}.$$

$\mu_0$ is the permeability of free space;
I is the filament current;
$(r_0, \theta_0)$ defines the coil geometry with respect to an arbitrary origin;
$(r, \theta)$ is the field point with respect to the origin; and
$P_n^m (\cos \theta)$ is the associated Legendre polynomial evaluated at the appropriate location in space.

The corresponding field expansion for points lying in the external region defined for $r>r_0$ is given by:

$$B_z(r > r_0, \theta) = I \sum_{n=1}^{\infty} b_n \frac{P_{n+1}(\cos\theta)}{r^{n+2}}, \quad (2)$$

where $$b_n = -\frac{\mu_0}{2}\sin\theta_0 P_n^1(\cos\theta)_0 r_0^{n+1}.$$

Further details of such equations are described in Edminister, J. A., Theory and problems of Electromagnetics. 1979: McGraw-Hill Book Company.

The equations (1) and (2) can be extended to calculate the magnetic field generated by a rectangular cross-section solenoid conductor as:

$$B_z\left(r < \sqrt{y_2^2 + z_2^2}, \theta\right) = I\sum_{n=1}^{\infty} \alpha_n P_{n-1}(\cos\theta) r^{n-1}, \quad (3)$$

$$B_z\left(r > \sqrt{y_1^2 + z_1^2}, \theta\right) = I\sum_{n=1}^{\infty} \beta_n \frac{P_{n+1}(\cos\theta)}{r^{n+2}},$$

where $$\alpha_n = -\frac{\mu_0}{2}\int_{z_2}^{z_1}\int_{y_2}^{y_1} \frac{y}{\sqrt{y^2+z^2}} \frac{P_n^1\left(\frac{z}{\sqrt{y^2+z^2}}\right)}{(y^2+z^2)^{\frac{n}{2}}} dy\,dz,$$

$$\beta_n = -\frac{\mu_0}{2}\int_{z_2}^{z_1}\int_{y_2}^{y_1} \frac{y}{\sqrt{y^2+z^2}} P_n^1\left(\frac{z}{\sqrt{y^2+z^2}}\right)(y^2+z^2)^{\frac{n+1}{2}} dy\,dz.$$

In equation (3) coordinates $(y_1, z_1)$ and $(y_2, z_2)$ define a rectangular conductor cross-section in the yz-plane as shown in FIG. 5. The harmonic coefficients $\alpha_n$ and $\beta_n$ can be computed analytically or numerically. In one example, the analytic expressions for the coefficients are obtained by solving the given integral for $\alpha_n$ and $\beta_n$, although alternatively Gaussian quadrature can be used to obtain the individual values of $\alpha_n$ and $\beta_n$, and typically this procedure is both accurate and efficient, when compared to the analytic expressions. Nevertheless, the first two harmonic coefficients for the inner region given in analytical form are:

$$\alpha_1 = -\frac{\mu_0}{2}\left[z_1\ln\left(\frac{y_2+\sqrt{y_2^2+z_1^2}}{y_1+\sqrt{y_1^2+z_1^2}}\right) + z_2\ln\left(\frac{y_1+\sqrt{y_1^2+z_2^2}}{y_2+\sqrt{y_1^2+z_2^2}}\right)\right],$$

$$\alpha_2 = -\frac{\mu_0}{2}\left[y_1\left(\frac{1}{\sqrt{y_1^2+z_2^2}} - \frac{1}{\sqrt{y_1^2+z_1^2}}\right) - y_2\left(\frac{1}{\sqrt{y_2^2+z_2^2}} - \frac{1}{\sqrt{y_2^2+z_1^2}}\right)\right] -$$
$$\frac{\mu_0}{2}\ln\left(\frac{\left(y_1+\sqrt{y_1^2+z_1^2}\right)\left(y_2+\sqrt{y_2^2+z_2^2}\right)}{\left(y_1+\sqrt{y_1^2+z_2^2}\right)\left(y_2+\sqrt{y_2^2+z_1^2}\right)}\right),$$

and for the outer region:

$$\beta_1 = -\frac{\mu_0}{2}\left[\frac{1}{3}(y_1^3 - y_2^3)(z_2 - z_1)\right],$$

$$\beta_2 = -\frac{\mu_0}{2}\left[\frac{1}{2}(y_1^3 - y_2^3)(z_2^2 - z_1^2)\right].$$

For the purpose of this example, the process is performed in two primary stages.

This first stage is to determine an initial layout of the superconducting coils and the associated current densities in a predefined domain subject to constraints, such as the homogeneity of the DSV and the size of the magnet stray field. This is achieved by changing the size of the magnet domain and by adjusting the number of internal and external harmonic coefficients to be vanished.

The second stage is the refinement of coil geometries to enhance the field homogeneity, to decrease the stray field (or fringe field) of the magnet and to restrict peak field values at the coils to an acceptable range.

Figure 6:
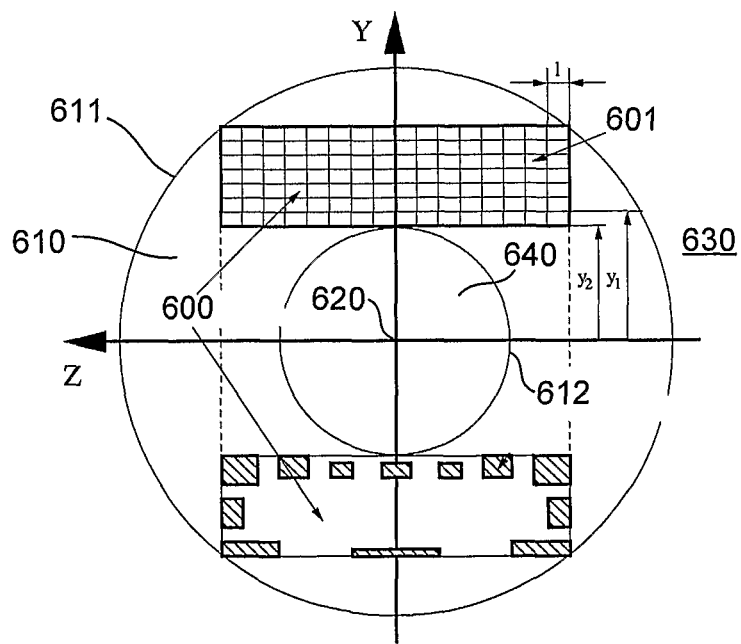
FIG. 6 is a schematic representation of regions used in determining a magnet arrangement.

To allow for the calculation of the magnetic field using the spherical harmonic method, the regions are typically configured as shown in FIG. 6.

In this example, the magnet region 600 lies within a region 610 centred at an origin 620. For this example, the region 610 has substantially spherical shell shape. However, as will be apparent from the remaining description, this is not essential, and any desired shape of region and magnet region can be employed using this method.

The stray field region 630 is positioned externally to an outer boundary 611 of region 610, while the imaging region 640 is positioned internally within an inner boundary 612 of region 610.

The domain of interest is divided into K small elements 601, as shown in the upper representation of the magnet region 600 in FIG. 6. The current densities $I_k$ associated with individual elements are then determined by minimizing the cost function $F_{init}$, which is formulated as a stored energy sum:

$$\min_{I_k} F_{init} = \frac{1}{2}\sum_{k=0}^{K-1} L_k I_k^2 A_k^2, \quad (4)$$

subject to:

$$\sum_{k=0}^{K-1} \alpha_{k,1} I_k = B_0, \quad (5)$$

$$\sum_{k=0}^{K-1} \alpha_{k,n} I_k = 0, \quad n = 2 \ldots N,$$

$$\sum_{k=0}^{K-1} \beta_{k,m} I_k = 0, \quad m = 1 \ldots M,$$

$I_{min} < I \leq I_{max}$, where $$L_k = \frac{31.6\left(\frac{(y_{k,1} - y_{k,2})y_{k,2}I_k}{A_k}\right)^2}{6y_{k,2} + 9l_k + 10(y_{k,1} - y_{k,2})} 10^{-6}, \quad (6)$$

and $B_0$ is the desired magnetic field strength at the iso-centre;
$\alpha_{k,n}$ and $\beta_{k,m}$ are the spherical harmonic terms of element k;
M specifies the number of external harmonic coefficients;
N specifies the number of internal harmonic coefficients, given that K≥M+N;
$L_k$ is the inductance of element k with its dimensions shown in FIG. 6; and
$A_k$ is the cross-sectional area of a single wire element.

The values chosen for M and N help define the size of the stray field and the DSV, respectively. M and N are increased to reduce the size of the stray field and to increase the size of the DSV. If a magnet design has N−1 internal coefficients and M external coefficients vanished, it is referred to as an N order M degree magnet design.

For magnet configurations in which coils are coaxial and symmetric about the illustrated xy-plane, the spherical harmonic expansion results in the elimination of all even order terms within the expansion. To further reduce computational complexity, the strategy employed here considers only one quarter of the magnet domain embedded within the computations and the constraint (5) is simplified as follows:

$$\sum_{k=0}^{K-1} \alpha_{k,1} I_k = \frac{B_0}{2}, \quad (7)$$

$$\sum_{k=0}^{K-1} \alpha_{k,2n+1} I_k = 0, \quad n = 1 \ldots \frac{N}{2} - 1,$$

$$\sum_{k=0}^{K-1} \beta_{k,2m+1} I_k = 0, \quad m = 0 \ldots \frac{M}{2} - 1,$$

$$I_{min} < I \le I_{max},$$

where, K is the number of elements in one quarter of the magnet domain.

The cost function defined in equation (4) is formulated to ensure that the stored energy within the coils is minimized, and consequently magnet training and quenching strains will be kept to a minimum. The formulated cost function also provides the benefit of minimizing the amount of superconducting wire used in the design, since the coil inductance is proportional to the conductor volume when restrictions on the length of the magnet domain are enforced.

In one example, the cost function $F_{init}$ is solved using the general quadratic program (QP) Nocedal, J. and S. J. Wright, *Numerical Optimization*. 2nd ed. 2006, New York: Springer. The problem is stated as a strictly convex QP, since $L_k$>0 and hence, the solution obtained using this procedure yields the global minimum, or the derived total stored energy has the smallest value. However, any other suitable optimization technique may also be used.

As previously described, this allows designs to be obtained that are unique and cannot be improved using other methodologies for this particular stored energy formulation. This stage of the magnet design process enables the generation of unique current density maps, named the minimum stored energy (MSE) current density map, in which the coils are embedded.

At the end of the initial layout stage, a current density map is obtained that has several local maxima and minima within the magnet domain referred to as extremities. The number of extremities is proportional to the number eliminated spherical harmonics, and notably these extreme points are distributed along the boundary or perimeter of the magnet domain.

The next step is to establish and refine the superconducting coil geometries to enhance the magnetic field homogeneity in the inner field, as well as, to satisfy other constraint requirements, including the peak magnetic field condition on the superconducting coils and the stray magnetic field strength.

Superconducting coils are placed in the magnet domain, based on the positioning of extremities in the form of local positive maxima and local negative minima. The coils are initially overlapped on the extreme point locations with their initial cross sectional areas being proportional to the value of the overlapping current densities. This process of identifying and locating coils will be described in more detail below.

After this step, the constant current coil geometries are refined by using a non-linear optimization method that minimizes the cost function $F_{refine}$ defined similarly as $F_{init}$:

$$\min_{I, L_k(y_{k,1}, y_{k,2}, z_{k,1}, z_{k,2})} F_{refine} = \frac{I^2}{2} \sum_{k=0}^{K-1} A_k^2 L_k, = \quad (8)$$

$$\frac{I^2}{2} \sum_{k=0}^{K-1} \frac{31.6 y_{k,2}^2 (y_{k,1} - y_{k,2})^2 (z_{k,1} - z_{k,2})^2}{6 y_{k,2} + 9(z_{k,1} - z_{k,2}) + 10(y_{k,1} - y_{k,2})} 10^{-6},$$

subject to:

$$I \sum_{k=0}^{K-1} \alpha_{k,1} = B_0, \quad (9)$$

$$I \sum_{k=0}^{K-1} \alpha_{k,n} = 0, \quad n = 2 \ldots N,$$

$$I \sum_{k=0}^{K-1} \beta_{k,m} = 0, \quad m = 1 \ldots M,$$

$$0 < I \le I_{max},$$

where, K is the number of the superconducting coils in the magnet domain.

As coils are coaxial and symmetric about the xy-plane, the computational complexity is reduced, and only one quarter of the magnet domain is considered. Constraint (9) in this case therefore becomes:

$$I \sum_{k=0}^{K-1} \alpha_{k,1} = \frac{B_0}{2}, \quad (10)$$

$$I \sum_{k=0}^{K-1} \alpha_{k,2n+1} = 0, \quad n = 1 \ldots \frac{N}{2} - 1,$$

$$I \sum_{k=0}^{K-1} \beta_{k,2m+1} = 0, \quad m = 0 \ldots \frac{M}{2} - 1,$$

$$0 < I \le I_{max},$$

where, K is the number of the superconducting coils in one quarter of the magnet domain.

It should be noted that for the purpose of this example, within the optimization process the current densities are positive and are the same for all elements, and hence for the coils. However, if required, the optimization process can also be used when different current densities on different coils are needed. The sign of the current in a particular coil is implied by the order of the $y_1$ and $y_2$ coordinates, as shown in FIG. 5. If $y_1 > y_2$, then the current has a positive sign, otherwise it has a negative sign. The need for negative currents within the computations is eliminated by using such an approach.

Additionally, similar results can be obtained taking into account mutual inductance. In this instance, this can be modelled by substituting equation (8) above for the following equation:

$$\min_{l(=l_k=l_l),M_{kl}} F_{refine} = \frac{1}{2}\sum_{k=0}^{K-1}\sum_{l=0}^{K-1} M_{kl}(A_k I_k)(A_l I_l),$$

where $M_{kl}$ is either self or mutual inductance.

In the initialisation of the coils, or to obtain the initial layouts using $F_{init}$, linear constraints were used. In the refinement stage, $F_{refine}$ is a constrained non-linear optimization problem that requires the use of an appropriate non-linear optimization algorithm to obtain the coil layout. One of the most effective methods of obtaining solutions to nonlinearly constrained optimization problems is to generate and solve quadratic sub-problems. For this reason, sequential quadratic programming (SQP) Lawrence, C., J. L. Zhou, and A. L. Tits, *User's Guide for CFSQP Version 2.5: A C Code for Solving (Large Scale) Constrained Nonlinear (Minimax) Optimization Problems, Generating Iterates Satisfying All Inequality Constraints*. 1997, University of Maryland) is implemented to solve the problem. The SQP method is a local optimization algorithm, which can give a globally optimal solution given suitable initial starting values. However, it will be appreciated that other suitable optimization techniques can be used.

Through the optimization process the individual coil dimensions and spatial locations are altered to achieve a better minimized solution, since $L_k$ is a function of coil geometry.

During the calculation iterations coil overlap is avoided by dividing the magnet domain into several layers and extra geometrical constraints based on the current density map are introduced to limit the movement of the coils. This step is fundamentally correct, since the current density maps do not suggest that the coils should be overlapped. In particular, limits on the y-coordinate of the individual coils are imposed by breaking the domain into layers, and large axial movements are restricted by imposing z-coordinate bounds.

Figure 7:
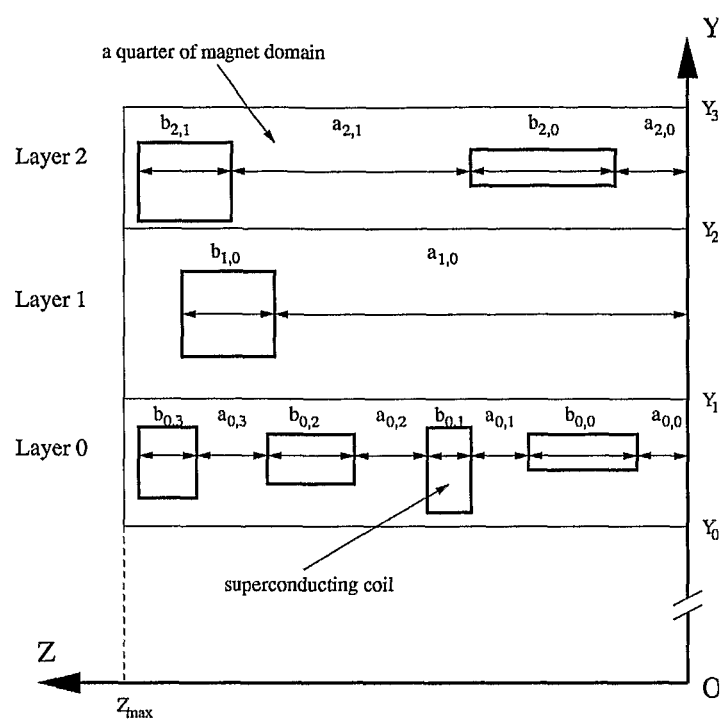
FIG. 7 is a schematic representation of the magnet geometries used in optimising a magnet arrangement.

An example of a particular layout of coils in the optimization stage is shown in FIG. 7.

In this example, a three layer configuration is shown, although this is for the purpose of example only, and any suitable number of coil layers can be provided. Each of the layers has respective boundaries provided at distances $Y_0$, $Y_1$, $Y_2$, $Y_3$ from the origin. The coils are generally designated $b_{l,p}$, where l is a layer identifier, and p is a coil number. The separation between the coils within each layer are generally designated $a_{l,p}$ associated with coil p for a particular layer l. The values for $a_{l,p}$ and $b_{l,p}$ must be non-negative, and in any given layer the sum of them must not be larger than the half length of the domain.

As discussed above, the extreme current densities are distributed over the domain boundary, hence, the upper and lower layers can have multiple coils and any layers between them consist of a single coil.

After convergence has been achieved the magnetic field at the superconducting coils is calculated using available methods, such as outlined in Forbes, L. K., S. Crozier, and D. M. Doddrell, *Rapid Computation of Static Fields Produced by Thick Circular Solenoids*. IEEE Transactions on Magnetics, 1997. 33(5): p. 4405-4410.

The magnetic fields are then tested for peak field criteria. If within the coils the peak field is greater than the allowable limit, then the individual layers are adjusted, such that the spacing between the coils is increased. For example as shown in FIG. 7, for the depicted three layer configuration, $Y_1$ and $Y_2$ are changed such that $|Y_2-Y_1|$ is increased. The optimization process is then repeated to obtain the new coil layouts according to the new layer constraints. It may happen that this process of iterative refinement needs to be repeated two or three times to ensure that the best coil layout can be obtained, for a given maximum level of peak magnetic field for the coils.

Example resulting configurations for different size and configurations of MRI systems will to now be described.

Both unshielded and shielded magnets are designed using the outlined strategy to generate the inner field, and also, to gauge the stray field produced by the magnets. The results are also used to illustrate the location of the MSE current density map extremities and alterations to these extremities as the size of the magnet domain is varied.

FIGS. 8A and 8B show 3D and 2D MSE current density profiles with contours for 3 m long magnet domains for unshielded order 10 degree 0 configurations, whilst equivalent shielded order 10 and degree 2 configurations are shown in FIGS. 9A and 9B.

Comparison of FIGS. 8 and 9 show that as the shielding is incorporated into the design, the extremities or the second stage coil locations wrap around the perimeter of the magnet domain to achieve a desired level of stray field. Both designs of FIGS. 8 and 9 aim to achieve the same DSV size, but the magnet of FIG. 9 would have a significantly smaller practical footprint due to the significantly smaller stray field.

It is notable that the current density maps of FIG. 8 do not have any negative values, whereas in FIG. 9 a negative minima is incorporated, which assists in providing the reduced footprint. This finding explains the reason why in lengthy, small DSV magnets, the winding directions are only in the positive sense, and negative winding coils are added if shielding is considered.

As the dimensions of the magnet domain are decreased, the current density minima start to take on negative values, which imply that negative winding direction coils are required to reduce the magnet length, as shown in FIGS. 10 and 11.

In this regard, FIGS. 10A and 10B show 3D and 2D MSE current density profiles with contours for unshielded order 14 degree 0 2 m length magnet domains, with 1 m length domains being shown in FIGS. 11A and 11B.

As shown in FIGS. 10A and 10B, if the magnet domain is sufficiently long, then the extremities may only be positioned on the lower domain boundary. The effect of decreasing the domain length is shown in FIG. 11. As can be seen by comparing FIGS. 10 and 11, the extremities within the magnet domain still alternate in current direction, but wrap around the perimeter of the domain. As a result for the unshielded magnet design, the individual coils are not restricted to the inner domain boundary, or bore perimeter, as it is generally referred to above.

Figure 12A:
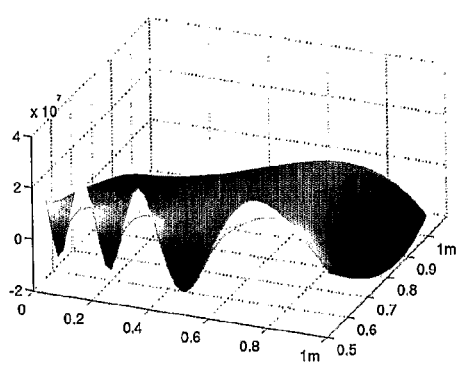
FIGS. 12A and 12B are 3D and 2D representations of examples of MSE current density profiles for shielded order 16 degree 4 2 m length magnet configurations.
Figure 12B:
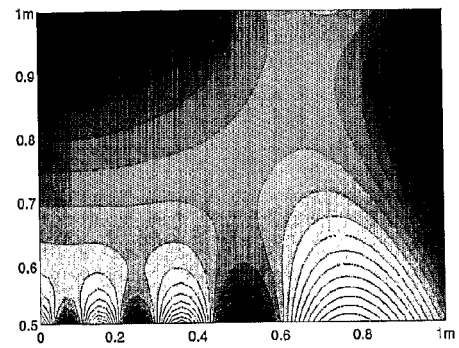
Figure 13A:
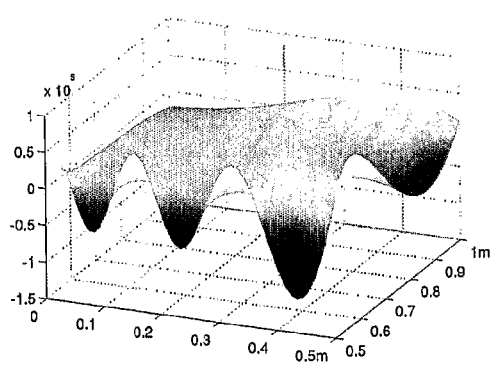
FIGS. 13A and 13B are 3D and 2D representations of examples of MSE current density profiles for shielded order 16 degree 4 1 m length magnet configurations.
Figure 13B:
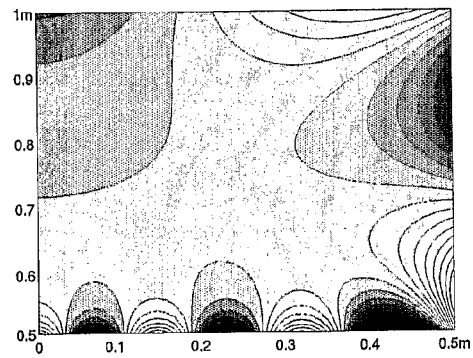

FIGS. 12A and 12B show 3D and 2D MSE current density profiles with contours for shielded order 16 degree 4 2 m length magnet domains, with 1 m length domains being shown in FIGS. 13A and 13B.

Similarly to FIG. 11, FIG. 13 provides the current density map for the shortened design. As can be seen in FIGS. 12 and 13 and according to the theory, the predicted coil layout due to the extreme current density values indicates alternating currents within the individual magnet coils. Once again, the current density map, as was in the case for the unshielded design, allocates the coils on the perimeter of the domain.

To obtain good stray field reduction in the design, it is necessary to increase the degree of the magnet, whereas to increase the DSV size, the order has to be increased. This fact will be more evident in the following sections, whereby the unshielded and shielded magnet arrangements for particular cases are outlined in more detail.

Short Bore Unshielded Magnet Design

In the following cases, the domain is limited in length to 1 m with bore diameter of 1 m, hence qualifying the designs as short MRI magnets. The superconducting wires used in the designs are taken from Sciver, S. W. V. and K. R. Marken, *Superconducting Magnets* Above 20 Tesla. Physics Today, 2002 (August): p. 37-42. All of the coils are formed using 1 mm×1 mm NbTi wires, by limiting the current to a level below 180A and the peak magnetic field on the superconducting coils to be less than 9 T.

An example of a resulting unshielded example configuration is shown in FIGS. 14A and 14B, which are 3D and 2D MSE current density profiles with contours for order 16 degree 0 magnet arrangements.

In this example, the resulting coil layout defined by the current density profile is shown in FIG. 14B. The allocation of the individual coils aligns with the current density map peaks, and the size of the coils is proportional to the magnitude of the current density at that location. In this manner, the initialised coils are reflective of the results obtained through the first initial layout stage.

The second optional optimisation stage is then seeded using the coil allocation of shown in FIG. 14B, and rapid convergence is achieved, due to the fact that the initial seed is highly accurate. Once the optimization of stage two has converged, by changing the location and size of the blocks, the resultant magnetic field is calculated.

An example of the final optimised magnet configuration and the resulting magnetic field is shown for the DSV in FIG. 15A and for the stray fields in FIG. 15B. In this example, the innermost contour corresponds to 1 ppm, followed by the 10 ppm contour, and the stray field with 5, 10, 15 and 20 gauss contour lines.

In this example, the DSV is 50 cm in diameter at the 1 ppm contour line, and approximately 56 cm in diameter to the 10 ppm contour line. The footprint of this unshielded magnet is quite large, as can be seen in FIG. 15B.

The final coil configuration of FIG. 15A and the corresponding coil numbering of FIG. 14B are given in Table 1 below.

In the table the $(y_c, z_c)$ centre coordinate of the individual coils is provided, with the number of coil windings defined as $(N_y, N_z)$ in the radial and axial directions, respectively. As can be seen in the table, the current in the coils is below the NbTi superconductor limit. The peak magnetic field on the superconducting coil was calculated to be 7.0741 T, which is also well below the required limit.

TABLE 1

| Coil | I (A) | $y_c$ (m) | $N_y$ | $z_c$ (m) | $N_z$ |
|---|---|---|---|---|---|
| 1 | −159 | 0.520532 | 29 | 0.012659 | 25 |
| 2 | 159 | 0.517828 | 36 | 0.061317 | 34 |
| 3 | −159 | 0.516825 | 34 | 0.122282 | 42 |
| 4 | 159 | 0.515187 | 30 | 0.190080 | 33 |
| 5 | −159 | 0.515190 | 30 | 0.265388 | 64 |
| 6 | 159 | 0.510032 | 12 | 0.352083 | 48 |
| 7 | −159 | 0.525500 | 51 | 0.454366 | 71 |
| 8 | 159 | 0.740900 | 118 | 0.449593 | 101 |

As was highlighted earlier, the final configuration for the unshielded case has an alternating current direction coil layout around the perimeter of the magnet domain. It should also be noted that the largest coil is actually not on the inner layer of the magnet (i.e. near the bore perimeter 202), but rather on an outer perimeter of the magnet region 200.

An increase in magnet domain length would see the outer layer disappear, and the upper coil would be inline with the other inner coils. Since both cases have the same order, their DSV dimensions are the same. However, the length of the magnet is shorter when outer coils are used in the design.

Short Bore Shielded Magnet Design

An example of an equivalent shielded case is shown in FIGS. 16A, 16B, 17A, 17B.

For the shielded magnet design, the external magnetic field harmonic coefficients are used to reduce the stray field, which means that the number of coils has to be increased to allow for appropriate magnetic field definition.

In the initial phase one stage, eighteen harmonics (order 14 degree 4) were included in the design to obtain a current density map as shown in FIG. 16A. The corresponding coil configuration for phase two of the optimization is illustrated in FIG. 16B, whereby the coils themselves are allocated on the perimeter of the magnet domain, and the size of the coils are proportional to the current density for that particular extreme current density. Independent of the design strategy, that is whether unshielded or shielded, the current within the coils alternates as highlighted earlier.

Table 2 provides the dimensions and locations of the final coil layout, after optimisation. The current in the NbTi wire is below the current carrying capability of the wire, and the peak field was calculated to be 8.9886 T, which is also below the peak magnetic field requirement.

The DSV and stray magnetic fields for the final coil layouts following optimisation are shown in FIGS. 17A and 17B respectively. In FIG. 17A, the innermost contour corresponds to 1 ppm, followed by the 10 ppm contour, whilst the stray field in FIG. 17B shows 5, 10, 15 and 20 gauss contour lines.

It can be seen from FIG. 17A that the DSV has a 40 cm diameter to the 1 ppm contour line and a diameter of 50 cm to the 10 ppm contour line. An important observation in this design is that the most outer coils do not necessarily have to be opposing current coils to reduce the stray field of the magnet, but rather, these coils are used in conjunction with the rest of the coils to obtain an overall effect satisfying both DSV and stray field requirements. Additionally, it can be seen from FIG. 17B that the stray field at the 5 gauss level extends no more than 4 m from the centre of the magnet.

TABLE 2

| Coil | I (A) | $y_c$ (m) | $N_y$ | $z_c$ (m) | $N_z$ |
|---|---|---|---|---|---|
| 1 | 159 | 0.523795 | 48 | 0.014565 | 29 |
| 2 | −159 | 0.530974 | 62 | 0.068407 | 61 |
| 3 | 159 | 0.522495 | 45 | 0.139960 | 59 |
| 4 | −159 | 0.531429 | 63 | 0.218645 | 79 |
| 5 | 159 | 0.548071 | 96 | 0.297088 | 29 |
| 6 | −159 | 0.537711 | 75 | 0.405162 | 83 |
| 7 | 159 | 0.783175 | 146 | 0.414818 | 170 |
| 8 | −159 | 1.087050 | 126 | 0.428726 | 143 |
| 9 | 159 | 1.115790 | 68 | 0.048344 | 97 |

A number of further designs are shown in FIGS. 18 to 21.

Short Bore Clinical 1.5T Magnet

FIGS. 18A and 18B show DSV fields with contours at 0.25, 1 and 10 ppm lines, and stray fields with contours at 5, 10, 15 and 25 gauss for a short bore clinical magnet. The properties of the resulting configuration are as follows:

Bore diameter: 1 m
Bore length: 1.28 m
DSV diameter at 1 ppm homogeneity: 50 cm

Stray Field (5G): 2.8 m (axial) 2.6 m (radial)
Symmetrical Magnet: B0=1.5 T, Bpeak=7.5938 T, I=175 MA/m2
Zmax=0.64 m, Ymax=0.95 m, Ymin=0.5 m
Short Bore Clinical 3.0T Magnet FIGS. 19A and 19B show DSV fields with contours at 0.25, 1 and 10 ppm, and stray fields with contours at 5, 10, 15 and 25 gauss for a short bore 3.0T clinical magnet. The properties of the resulting configuration are as follows:
Bore diameter: 1 m
Bore length: 1.44 m
DSV diameter at 1 ppm homogeneity: 50 cm
Stray Field (5G): 3.1 m (axial) 2.8 m (radial)
Symmetrical Magnet: B0=3 T, Bpeak=8.2580 T, I=175 MA/m2
Zmax=0.72 m, Ymax=1.01 m, Ymin=0.5 m
Active Shield 7.0T Magnet FIGS. 20A and 20B show DSV fields with contours at 0.25, 1 and 10 ppm, and stray fields with contours at 5, 10, 15 and 25 gauss for a high field clinical magnet. The properties of the resulting configuration are as follows:
Bore diameter: 1 m
Bore length: 1.8 m
DSV diameter at 1 ppm homogeneity: 50 cm
Stray Field (5G): 4.45 m (axial) 3.85 m (radial)
Symmetrical Magnet: B0=7 T, Bpeak=10.5124 T (Nb3Sn), I=175 MA/m2
Zmax=0.9 m, Ymax=1.0 m, Ymin=0.5 m
Open 1.0T Magnet
FIGS. 21A and 21B show DSV fields with contours at 0.25, 1 and 10 ppm, and stray fields with contours at 5, 10, 15 and 25 gauss for an open bore clinical magnet. The properties of the resulting configuration are as follows:
Gap: 60 cm
Pole length: 0.4 m
Total length: 1.44 m
DSV diameter at 1 ppm homogeneity: 50 cm
Stray Field (5G): 3.5 m (axial) 3.1 m (radial)
Open Magnet: B0=1 T, Bpeak=7.9319 T, I=175 MA/m2
Zmax=0.7 m, Zmin=0.3 m, Ymax=1.0 m, Ymin=0.5 m Accordingly, the above described processes provide a method of designing magnet arrangements, and in particular for designing superconducting magnet arrangements suitable for use in MRI imaging apparatus. The processes have the ability to arrange coils in a manner that ensures that the overall dimensions and stored magnetic energy are minimized with peak current and peak magnetic field in acceptable ranges.

In one example, the process uses a magnet region or domain that is treated as current density maps, in which, superconducting coils are embedded. The current density maps from which the coils themselves are derived are unique, and allow a minimum stored energy configuration to be derived.

In one example, a second optimisation phase may also then be performed to generate final coil layouts that take into account coil dimensions for required field linearity, and peak and stray field minimization.

The results suggest that coils should be placed around the perimeter of the domain with adjacent coils having alternating winding directions for best design performance.

The techniques can be used to derive unshielded and shielded designs, both of which yield magnet configurations that allocate coils around the perimeter of the magnet domain. For the unshielded case different order and zero degree implementations can be used, and the degree is varied to achieve certain shielding requirements for the designs. Irrespective of the shielding requirements, the coils themselves tend to be placed on the boundaries of the current density map domain, with the current direction alternating between adjacent coils.

The stray field of the shielded magnet designs are very small whilst maintaining a large DSV, when compared to the overall magnet dimensions.

Whilst the above examples have focused on spherical DSV magnets, this is not essential, and similar techniques can be used for any desired field configuration.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A magnet arrangement for use in magnetic resonance imaging apparatus, the magnet arrangement including a number of current carrying coils arranged substantially around a perimeter of a magnet region at least partially surrounding a bore, and wherein, for current carrying coils on a bore perimeter of the magnet region, the bore perimeter being adjacent the bore, each current carrying coil carries a current in an opposing direction to each adjacent coil on the bore perimeter,
wherein the magnet generates a desired field within at least one of:
an imaging region; and,
a stray field region,
and
wherein the homogeneity has a variation of less than at least one of:
100 ppm;
20 ppm; and,
10 ppm.

2. A magnet arrangement for use in magnetic resonance imaging apparatus, the magnet arrangement including a number of current carrying coils arranged substantially around a perimeter of a magnet region at least partially surrounding a bore, and wherein, for current carrying coils on a bore perimeter of the magnet region, the bore perimeter being adjacent the bore, each current carrying coil carries a current in an opposing direction to each adjacent coil on the bore perimeter,
wherein the magnet region has an arbitrary shape positioned relative to at least one of:
a bore; and,
an imaging region,
wherein the magnet region is rotationally symmetric with respect to a field axis,
wherein the field axis is aligned with a bore axis, and
wherein a stray field region substantially surrounds the magnet region.

3. A magnet arrangement for use in magnetic resonance imaging apparatus, the magnet arrangement including a number of current carrying coils arranged substantially around a perimeter of a magnet region at least partially surrounding a bore, and wherein, for current carrying coils on a bore perimeter of the magnet region, the bore perimeter being adjacent the bore, each current carrying coil carries a current in an opposing direction to each adjacent coil on the bore perimeter,
wherein the magnet region has an arbitrary shape positioned relative to at least one of:
a bore; and,
an imaging region, wherein the magnet region is rotationally symmetric with respect to a field axis, wherein the field axis is aligned with a bore axis, wherein the imaging region has a substantially spherical shape positioned on a field axis radially inwardly of the magnet region, and wherein a stray field region is positioned on the field axis radially outwardly of the magnet region.

4. A magnet arrangement for use in magnetic resonance imaging apparatus, the magnet arrangement including a number of current carrying coils arranged substantially around a perimeter of a magnet region at least partially surrounding a bore, and wherein, for current carrying coils on a bore perimeter of the magnet region, the bore perimeter being adjacent the bore, each current carrying coil carries a current in an opposing direction to each adjacent coil on the bore perimeter, wherein the magnet region has an arbitrary shape positioned relative to at least one of:

a bore; and, an imaging region, wherein the magnet region is rotationally symmetric with respect to a field axis, wherein the field axis is aligned with a bore axis, wherein the imaging region has a substantially spherical shape positioned on a field axis radially inwardly of the magnet region, and wherein the desired field has a field strength of less than a selected amount within a stray field region.

5. A magnet arrangement for use in magnetic resonance imaging apparatus, the magnet arrangement including a number of current carrying coils arranged substantially around a perimeter of a magnet region at least partially surrounding a bore, and wherein, for current carrying coils on a bore perimeter of the magnet region, the bore perimeter being adjacent the bore, each current carrying coil carries a current in an opposing direction to each adjacent coil on the bore perimeter, wherein the magnet generates a desired field within at least one of:

an imaging region; and, a stray field region, and wherein the homogeneity has a variation of less than at least one of:

100 ppm;

20 ppm; and, 10 ppm, and wherein the selected amount is less than, at least one of:

20 Gauss;

10 Gauss; and,

5 Gauss.

* * * * *